United States Patent [19]
Fischetti et al.

[11] Patent Number: 5,997,862
[45] Date of Patent: Dec. 7, 1999

[54] THERAPEUTIC TREATMENT OF GROUP A STREPTOCOCCAL INFECTIONS

[75] Inventors: Vincent Fischetti, West Hempstead, N.Y.; Lawrence Loomis, Columbia, Md.

[73] Assignee: New Horizons Diagnostics Corporation, Columbia, Md.

[21] Appl. No.: 08/962,523

[22] Filed: Oct. 31, 1997

[51] Int. Cl.$^6$ ..................................................... A61K 38/43
[52] U.S. Cl. .......................... 424/94.1; 424/441; 424/440; 424/439; 424/434; 424/464; 424/489; 424/45; 514/2; 514/937; 514/944; 514/948
[58] Field of Search ........................... 424/45, 94.1, 441, 424/439, 440, 434, 464, 489; 435/7.34; 514/2, 937, 944, 948

[56] References Cited

U.S. PATENT DOCUMENTS 5,604,109  2/1997  Fischetti et al. ........................ 435/7.34

*Primary Examiner*—Raj Bawa
*Attorney, Agent, or Firm*—Jonathan E Grant, Grant Partent Services

[57] ABSTRACT

The present invention relates to an oral delivery system containing a group c streptococcal phage associated lysin enzyme for the prophylactic and therapeutic treatment of Streptococcal A throat infections, commonly known as strep throat.

26 Claims, No Drawings

THERAPEUTIC TREATMENT OF GROUP A STREPTOCOCCAL INFECTIONS

BACKGROUND OF THE INVENTION

1. Field of the Invention

The present invention relates to an oral delivery means, such as a candy, chewing gum, lozenge, troche, tablet, a powder, an aerosol, a liquid or a liquid spray, containing a group C streptococcal phage associated lysin enzyme for the prophylactic and therapeutic treatment of Streptococcal A throat infections, commonly known as strep throat.

2. Description of the Prior Art

Group A streptococci have been shown to be an important pathogen capable of existing both in a carrier state in an asymptomatic individual and in a symptomatic individual with symptoms of disease ranging from a mild sore throat, tonsillitis, or impetigo. If untreated these streptococcal infections could lead to glomerulonephritis, rheumatic fever and possibly permanent rheumatic heart disease. With the advent of antimicrobial agents, specifically penicillin derived antibiotics, the causative organism can be readily eliminated following the prescribed regimen of appropriate antibiotic therapy.

The fact that an infected individual (usually children & young adults) can pass group A streptococcal organisms to others, particularly in daycare centers and schools, necessitates the isolation of the known infected individual away from these environments for at least 24 to 72 hours after antimicrobial therapy has been initiated. It has been shown in controlled studies that early detection and appropriate treatment results in a reduction in the overall pattern of cyclic transmission of the troublesome pathogen as well as a reduction or elimination of the sequelae of group A infections (rheumatic fever or nephritis).

The first individual to identify the serological and immunological groups of streptococci was Dr. Rebecca Lancefield, (Lancefield, R. C., "A Serological Differentiation of Human and other Groups of Hemolytic Streptococci," J. Exp. Med., Vol. 57, pp 571–595 1933), after whom the grouping system was named. The group A streptococcus was identified on the basis of B-1, 4 N-acetylglucosamine terminal sugar moieties on a repeating rhamnose sugar backbone found as part of the structure of the organism's cell wall. Antiserum raised against group A streptococci and subsequent absorptions to remove cross-reactions were shown to specifically react with the cell wall component of these organisms and became the grouping antisera for group A streptococci. A number of methods have been devised to fragment the group A streptococcal cell wall carbohydrate. These methods include heating by boiling at pH 2.0, autoclaving, trichloroacetic acid extraction, hot formamide digestion, nitrous acid extraction and enzyme digestion by enzymes derived from the soil microorganisms of species streptomyces, and the phage-associated enzyme lysin. Each of these methods have various advantages and disadvantages.

The rapid diagnosis of group A streptococcal pharyngitis has become more readily available to both physicians and clinical laboratories by replacing time consuming culturing methods requiring a minimum of 24 to 72 hours to identify the presence of group A streptococci with a rapid antigen-antibody test capable of being performed and read in less than one hour. Culturing methods vary in the degree of sensitivity of detection. In one case, a simple 5% sheep blood agar plate may be used in conjunction with a Bacitracin disc and culturing 24 hours at 37 degree(s) C. aerobically to identify group A streptococci. Alternatively, a selective media and anaerobic conditions may be used to inhibit overgrowth by other organisms and incubation at 35 degree(s) C. for a minimum of 48 hours. In addition, depending on the transport media, the delay in testing, and any antibacterial agents that the patient may have taken, culturing may result in nonviable organisms that fail to grow in the media although the patient is indeed colonized by the group A streptococcus. In the latter case a sensitive immunoassay for group A streptococcal antigen can detect these nonviable organisms.

The sensitivity of the immunoassay procedure is effected by the amount of group A streptococcal carbohydrate antigen released and recognized by the specific immunological reagent. Enzymatic digestion by enzymes such as that produced by the species streptomyces, have proven to be quite effective in antigen release over some chemical methods and micro-nitrous acid but the poor specific activity and the presence of proteases makes it slow and incompatible for prolonged contact with immunological reagents. Maxted, (Maxted, W. R., "The Active Agent in Nascent Phage Lysis of Streptococci," J. Gen Micro, vol 16, pp 585–595 1957), Krause, (Krause, R. M., "Studies on the Bacteriophages of Hemolytic Streptococci," J. Exp Med, vol 108, pp 803–821 1958), and Fischetti, (Fischetti, V. A., et al, "Purification and Physical Properties of Group C Streptococcal Phage Associated Lysin," J. Exp Med, Vol 133 pp 1105–1117 1971, have reported the characteristics of an enzyme produced by the group C streptococcal organism after being infected with a particular bacteriophage identified as C1. The enzyme was given the name lysin and was found to specifically cleave the cell wall of group A, group C and group E streptococci. These investigators provided information on the characteristics and activities of this enzyme with regards to lysing the group A streptococci and releasing the cell wall carbohydrate. They never reported on the utility of this enzyme in an immunological diagnostic test for the detection of group A streptococci from throat swabs in patients. The failure to use this enzyme for a clinical diagnostic test was due to a number of problems associated with the enzyme such as: the difficulty in growing large amounts of bacteriophage in the group C streptococci, the time delays in inactivating the residual enzyme when trying to obtain phage stocks, the instability of the enzyme itself to oxidative conditions and heat, and nonspecific reactions in immunoassays performed in the presence of other organisms and the biological components in the sample.

U.S. Pat. No. 5,604,109 (Fischetti et al.) teaches the rapid and sensitive detection of group A streptococcal antigens by a diagnostic test kit which utilizes a sampling device consisting of a throat swab made of synthetic or natural fibers such as Dacron or rayon and some type of shaft which holds the fibers and which is long enough to place the fibers in the tonsillar area and capable of being used to swab the area to remove sufficient numbers of colonizing or infecting organisms. The swab can then be placed in the enzyme extraction reagent in several configurations and subsequently used in an immunoassay. The invention can comprise a test kit for detecting Group A streptococci, comprising an extraction reagent containing lysin enzyme for releasing Group A streptococcal components, and a ligand capable of binding with a component of the Group A streptococcus.

SUMMARY OF THE INVENTION

The present invention (which incorporates U.S. Pat. No. 5,604,109 in its entirety by reference) uses the lysin enzyme produced by the group C streptococcal organism after being infected with a particular bacteriophage (identified as C1) as either a prophylactic treatment for preventing those who have been exposed to others who have the symptoms of a strep infection from getting sick, or as a therapeutic treatment for those who have already become ill from the infection.

The lysin enzyme would be administered in the form of a candy, chewing gum, lozenge, troche, tablet, a powder, an aerosol, a liquid or a liquid spray.

The method for the treatment of streptococcus A exposure will comprise applying an effective dosage of a pharmaceutically acceptable amount of an extraction reagent comprising Group C streptococcal phage associated lysin enzyme to the oral mucosa of a mammal in need of treatment, permitting the extraction reagent to remain in contact with the oral mucosa for a period of time necessary for the lysin enzyme to saturate the oral mucosa; and applying additional dosages of such the lysin enzyme in like fashion until treatment is complete.

The present invention is based upon the discovery that phage lysin can effectively and efficiently break down the cell wall of Group A Streptococci and the resultant antigenic fragments are reactive with antibodies specific for the Group A Streptococcal carbohydrate. The semipurified enzyme is lacking in proteolytic enzymatic activity and therefore non-destructive to specific antibodies when present during the digestion of the bacterial cell wall.

DETAILED DESCRIPTION OF THE INVENTION

This invention discloses the use of the lysin enzyme produced by the group C streptococcal organism after being infected with a particular bacteriophage (identified as C1) as either a prophylactic treatment for preventing those who have been exposed to others who have the symptoms of a strep infection from getting sick, or as a therapeutic treatment for those who have already become ill from the infection.

Means of application include, but are not limited to direct, indirect, carrier and special means or any combination of means. Direction application of the lysin enzyme may be by nasal sprays, nasal drops, nasal ointments, nasal washes, nasal injections, nasal packings, or indirectly through use of throat lozenges, or through use of mouthwashes or gargles, or through the use of ointments applied to the nasal nares, the bridge of the nose, or the face or any combination of these and similar methods of application. The forms in which the lysin enzyme may be administered include but are not limited to lozenges, troches, candies, injectants, chewing gums, tablets, powders, sprays, liquids, ointments, and aerosols.

Prior to, or at the time the enzyme is put in a carrier system, the enzyme may be in a phosphate buffer environment for maintaining a pH range between about 4.0 and about 8.0, more preferably between about 5.5 and about 7.5 and more preferably at about 6.1.

The stabilizing buffer should allow for the optimum activity of the lysin enzyme. The buffer may be a reducing reagent, such as dithiothreitol. The stabilizing agent may also be or include a metal chelating reagent, such as ethylenediaminetetraacetic acid disodium salt, or may also contain a citrate-phosphate buffer.

To prevent spoilage, the stabilizing buffer may also contain a bactericidal or bacteriostatic reagent as a preservative, such as a small amount of sodium benzoate.

The lozenge into which the lysin enzyme is added may contain any or all of the following ingredients: sugar, corn syrup, a variety of dyes, non-sugar sweeteners, flavorings, and any binders. Similarly, any gum based products may contain any or all of the following ingredients: acacia, carnauba wax, citric acid, corn starch, food colorings, flavorings, non-sugar sweeteners, gelatin, glucose, glycerin, gum base, shellac, sodium saccharin, sugar, water, white wax, and cellulose and other binders.

Lozenges may contain any or all of the following ingredients: sucrose, corn starch, acacia, gum tragacanth, anethole, linseed, oleoresin, mineral oil, and cellulose and other binders. In another embodiment of the invention, sugar substitutes are used in place of dextrose, sucrose, or other sugars.

Any of the carriers for the lysin enzyme may be manufactured by conventional means. However, it is preferred that any mouthwash or similar type products not contain alcohol to prevent denaturing of the enzyme. Similarly, when the lysin enzyme is being placed in a cough drop, gum, candy or lozenge during manufacture, such placement should be made prior to the hardening of the lozenge or candy but after the cough drop or candy has cooled somewhat, to avoid heat denaturation of the enzyme.

The enzyme may be added to these substances in liquid form or in a lyophilized state, whereupon it will be solubilized when it meets a liquid body. The enzyme may also be in a micelle or liposome.

The effective dosage rates of the use of the lysin enzyme will depend in part on whether the lysin will be used therapeutically or prophylactically, the duration of exposure of the recipient to the Streptococci, the size and weight of the patient, etc. The effective dosage comprises an amount which is sufficient to provide an enzyme concentration of between about 0.1 mM and 1 M in the saliva of the mammal being treated, or between about 1 mM and about 300 mM in the saliva of the mammal being treated, or between about 5 mM and about 50 mM in the saliva of the mammal being treated. While this treatment may be used in any mammalian species, the preferred use of this product is for a human.

EXAMPLE 1

The extraction reagent containing the group C phage lysin enzyme is prepared as follows:

Group C streptococcal strain 26RP66 (ATCC #21597) or any other group C streptococcal strain is grown in Todd Hewitt medium at 37 degree(s) C. to an OD of 0.23 at 650 nm in an 18 mm tube. Group C bacteriophage (C1) (ATCC #21597-B1) at a titer of $5\times10^6$ is added at a ratio of 1 part phage to 4 parts cells. The mixture is allowed to remain at 37 degree(s) C. for 18 min at which time the infected cells are poured over ice cubes to reduce the temperature of the solution to below 15 degree(s) C. The infected cells are then harvested in a refrigerated centrifuge and suspended in 1/300th of the original volume in 0.1M phosphate buffer, pH 6.1 containing $5\times10^{-3}$ M dithiotreitol and 10 $\mu$g of DNAase. The cells will lyse releasing phage and the lysin enzyme. After centrifugation at 100,000×g for 5 hrs to remove most of the cell debris and phage, the enzyme solution is aliquoted and tested for its ability to lyse Group A Streptococci.

The number of units/ml in a lot of enzyme is determined to be the reciprocal of the highest dilution of enzyme required to reduce the OD650 of a suspension of group A streptococci at an OD of 0.3 to 0.15 in 15 minutes. In a typical preparation of enzyme $4\times10^5$ to $4\times10^6$ units are produced in a single 12 liter batch.

Use of the enzyme requires a minimum number of units of lysin enzyme per test depending on the incubation times required. The enzyme is diluted in a stabilizing buffer containing the appropriate conditions for stability, maximum enzymatic activity. The preferred embodiment is to use a lyophilized reagent which can be reconstituted with water. The stabilizing buffer can comprise a reducing reagent, which can be dithiothreitol in a concentration from 0.001M to 1.0M, preferably 0.005M. The stabilizing buffer can comprise a metal chelating reagent, which can be ethylenediaminetetraacetic acid disodium salt in a concentration from 0.00001M to 1.0M, preferably 0.005M. The stabilizing buffer can comprise a citrate-phosphate buffer in a concentration from 0.001M to 1.0M, preferably 0.05M. The stabilizing buffer can have a pH value in the range of from about 4.0 to 8.0, preferably 6.1. The stabilizing buffer can comprise a bactericidal or bacteriostatic reagent as a preservative. Such preservative can be sodium azide in a concentration from 0.001 percent to 0.1 percent, preferably 0.02 percent.

The preparation of phage stocks for lysin production is the same procedure described above for the infection of phage and group C streptococcus in the preparation of the lysin enzyme. However, instead of pouring the infected cells over ice, the incubation at 37 degree(s) C. is continued for a total of 1 hour to allow lysis and release of the phage and also enzyme in the total volume. In order for the phage to be used for subsequent lysin production the residual enzyme must be inactivated or removed to prevent lysis from without of the group C cells rather than phage infection.

EXAMPLE 2

The enzyme prepared according to example 1 is diluted to a concentration of 100 units/ml in a buffer consisting of 0.05M citrate phosphate buffer pH 6.1 containing 0.1% rabbit immunoglobulin, 0.005M (ethylenedinitrilo) tetraacetic acid disodium salt (EDTA), 0.005M Dithiothreitol, 0.02% sodium azide, 0.01% N-acetylglucosamine. One part colloidal gold sol labelled with Group A Streptococcal Antibody (OD sup 520 1.5) suspended in 0.02M Tris buffer pH 8.2, 1.0% bovine serum albumin, 0.02% sodium azide, 300K units heparin, is added to 3 parts of the enzyme reagent, mixed, filtered through a 0.22 micron filter, and 200 microliters aliquoted per tube and lyophilized. This lyophilized reagent is stable at elevated temperatures (i.e. 45 degree(s) C.) for short term conditions (i.e. 2 weeks) and long term storage at room temperatures (>1 year).

EXAMPLE 3

Method

1. Start a day culture of group A streptococcal strain S43/192/39R (Streptomycin resistant) (from frozen blood broth); 500 μl in 50 ml of Todd Hewitt (TH) broth containing 1% yeast extract and 100 μl of Streptomycin/ml.

2. Grow to an OD$_{650}$ of 0.59

3. Centrifuge for 15 minutes at 3000 rpm to sediment bacteria.

4. Resuspend organisms in 1 ml volume of TH w/o antibiotics (3×10$^5$/100 μl as determined by plate count).

5. Add 0.5 of these concentrated cells to ) 0.5 ml of pH 6.1 phosphate buffer as a control.

6. Five minutes before administering to the mice, 0.5 ml of the concentrated cell suspension was mixed with 0.5 ml of phage lysin solution pre-diluted to 10,000 units/ml in pH 6.1 phosphate buffer.

Five mice received 60 μl of "control" solution divided equally orally and intranasally.

Five mice received 60 μl of lysin and bacteria mixture divided equally orally and intranasally.

Throat swabs were performed onto 5% sheep blood, proteose peptone agar plates containing 500 μg/ml of streptomycin. Plates were incubated overnight at 37° C.

The following results were obtained:

|  | Colony Forming Units | | | |
|---|---|---|---|---|
|  | 7/22<br>1d | 7/23<br>2d | 7/24<br>3d | 7/28<br>7d |
| LYSIN |  |  |  |  |
| L1 | 0 | 0 | 0 | 0 |
| L2 | 0 | 0 | 0 | 0 |
| L3 | 0 | 0 | 0 | 0 |
| L4 | 0 | 1 | 0 | 0 |
| L5 | 0 | 0 | 1 | 0 |
| CONTROL |  |  |  |  |
| C1 | 26 | 14 | 7 | 0 |
| C2 | >400 | 17 | 100 | 83 |
| C3 | 9 | 0 | 15 | 0 |
| C4 | >400 | >400 | >400 | 220 |
| C5 | 2 | 2 | 30 | 0 |

These results show that the contact between phage lysin and group A streptococci for as little as five minutes prevents the streptococci from colonizing the upper respiratory tract of the mice in this model system.

Each dose is kept in contact with the oral mucosa as long as necessary in order to improve performance over the original invention. Improved administration of the lysin enzyme to the oral mucosa may be by any means such as gargles, mouth rinses, lozenges, troches, chewing gums, candies, powders, and sprays, so long as it offers convenience, palatability, safety, or further reduction in the duration of or prevention of the effects of Streptococcus A exposure.

Many modifications and variations of the present invention are possible in light of the above teachings. It is, therefore, to be understood within the scope of the appended claims the invention may be protected otherwise than as specifically described.

What is claimed is:

1. A pharmaceutical composition for use in the treatment of a streptococcal infection, comprising:
    an effective amount of lysin enzyme produced by group C streptococcal bacteria infected with a C1 bacteriophage; and
    a carrier for delivering said lysin enzyme to a mouth, throat, or nasal passage.

2. The composition according to claim 1, wherein said carrier is selected from the group consisting of candy, chewing gum, lozenge, troche, tablet, powder, aerosol, liquid, liquid spray, nasal sprays and nasal ointments.

3. The composition according to claim 1, further comprising a buffer that maintains pH of the composition at a range between about 4.0 and 9.0.

4. The composition according to claim 3, wherein said buffer maintains the pH of the composition at range between 5.5 and 7.5.

5. The composition according to claim 3, wherein said buffer comprises a reducing agent.

6. The composition according to claim 5, wherein said reducing agent is dithiothreitol.

7. The composition according to claim 3, wherein said buffer comprises a metal chelating agent.

8. The composition according to claim 7, wherein said metal chelating agent is ethylenediaminetetraacetic disodium salt.

9. The composition according to claim 3, wherein said buffer is a citrate-phosphate buffer.

10. The composition according to claim 1, further comprising a bactericidal or bacteriostatic agent as a preservative.

11. The composition according to claim 1, wherein said lysine enzyme is lyophilized.

12. The composition according to claim 1, wherein said carrier further comprises a sweetener.

13. The composition according to claim 1, wherein said composition is used in the therapeutic treatment of streptococcal infections.

14. The composition according to claim 1, wherein said composition is used in the prophylactic treatment of streptococcal infections.

15. The composition according to claim 14, wherein said streptococcal infection is a streptococcal throat infection.

16. The composition according to claim 1, wherein said carrier is a candy.

17. The composition according to claim 1, wherein said carrier is a chewing gum.

18. The composition according to claim 1, wherein said carrier is a lozenge.

19. The composition according to claim 1, wherein said carrier is a troche.

20. The composition according to claim 1, wherein said carrier is a powder.

21. The composition according to claim 1, wherein said carrier is an aerosol.

22. The composition according to claim 1, wherein said carrier is a liquid spray.

23. The composition according to claim 1, wherein said carrier is a nasal spray.

24. The composition according to claim 1, wherein said mammal is a human.

25. The composition according to claim 1, wherein said carrier is suitable for delivering said lysin enzyme to the mouth and throat.

26. The composition according to claim 1, wherein said carrier is suitable for delivering said lysin enzyme to the nasal passage.

* * * * *